(12) United States Patent
Barben, II et al.

(10) Patent No.: US 6,416,653 B1
(45) Date of Patent: Jul. 9, 2002

(54) DEVICE FOR SEPARATING ELECTROLYTE CHAMBERS WITHIN AN ELECTROCHEMICAL SENSOR

(75) Inventors: Ted Barben, II; Harvey Mitchell, both of Carson City, NV (US)

(73) Assignee: Barben Analyzer Technology, LLC, Carson City, NV (US)

( * ) Notice: Subject to any disclaimer, the term of this patent is extended or adjusted under 35 U.S.C. 154(b) by 0 days.

(21) Appl. No.: 09/618,510

(22) Filed: Jul. 18, 2000

(51) Int. Cl.[7] ............................................. G01N 27/401
(52) U.S. Cl. ................. 205/787.5; 204/409; 204/420; 204/433; 204/435; 205/775
(58) Field of Search ................. 204/433, 435, 204/420, 409; 205/775, 787.5

(56) References Cited

U.S. PATENT DOCUMENTS

| | | | |
|---|---|---|---|
| 3,264,205 A | * | 8/1966 | Leonard et al. ............. 204/435 |
| 4,128,468 A | | 12/1978 | Bukamier |
| 4,252,124 A | | 2/1981 | Maurer |
| RE31,333 E | | 8/1983 | Barben, II |
| 4,477,330 A | | 10/1984 | Nielsen |
| 4,543,175 A | | 9/1985 | Subsara |
| 5,147,524 A | | 9/1992 | Broadley |
| 5,221,456 A | | 6/1993 | Benton |
| 5,346,606 A | | 9/1994 | Christner |
| 5,395,503 A | * | 3/1995 | Parce et al. .................. 204/409 |
| 5,516,413 A | | 5/1996 | Foster |
| 5,567,291 A | | 10/1996 | Melzer |
| 5,630,921 A | | 5/1997 | Hess |
| 6,054,031 A | | 4/2000 | Benton |

FOREIGN PATENT DOCUMENTS

EP 0351891 * 1/1990

* cited by examiner

Primary Examiner—T. Tung
(74) Attorney, Agent, or Firm—Thorpe North & Western LLP

(57) ABSTRACT

The present invention is drawn generally to an improved electrochemical sensor. The reference cell within the sensor can be a salt bridge comprising at least two chambers for containing an electrolyte fluid, preferably containing a semi-permeable plug impregnated with an electrolyte, an essentially fluid impermeable plug for separating the at least two chambers, and a narrow opening through the plug providing a non-axial flow path for ionic communication between the at least two chambers when the electrolyte fluid is present.

33 Claims, 2 Drawing Sheets

DEVICE FOR SEPARATING ELECTROLYTE CHAMBERS WITHIN AN ELECTROCHEMICAL SENSOR

FIELD OF THE INVENTION

The present invention is drawn to an electrochemical sensor. More specifically, a separation device having a non-axial flow path therethrough for use within a reference cell is disclosed.

BACKGROUND OF THE INVENTION

An electrochemical sensor used for measuring pH, ORP, or other specific ion concentrations is typically comprised of three parts: a specimen sensing ion electrode, a reference cell, and an amplifier that translates signal into useable information that can be read. For example, in the case of a pH sensor, the specimen sensing ion electrode can be a hydrogen ion sensitive glass bulb with a millivolt output that varies with the changes in the relative hydrogen ion concentration inside and outside of the bulb. Conversely, the reference cell output does not vary with the activity of the hydrogen ion.

The reference cell is the structure in which most problems can occur within an electrochemical sensor. The reference cell consists of essentially three parts: an internal element such as a metal-metal salt, e.g., Ag/AgCl, Pt/Hg$_2$Cl$_2$, etc., a filling solution such as an electrolyte, and a liquid junction through which the filling solution contacts the desired specimen to be measured.

Specifically, the reference cell is used to maintain a common electrical potential with the specimen fluid being measured. The filling solution or electrolyte provides the conductive bridge to the specimen fluid and surrounds the reference element with an electrochemically stable environment. In order to obtain an accurate reading, this liquid junction must be in place. In the ideal liquid junction, electrolytic contact between the reference element and specimen fluid would provide the necessary communication, and yet prevent mixing of the specimen fluid with the electrolyte. However, liquid junctions can not be perfect. This is because contact between the electrolyte and the specimen fluid is present in order for ion flow to occur, and thus, mixing can ultimately occur.

With earlier pH meters, the liquid junction was simply a minute opening in a glass or ceramic barrier through which ion communication between the two solutions could be established. However, with prolonged usage, the single opening junctions were found to become readily clogged. Thus, more recently, liquid junction designs have typically comprised of ceramic or other frit material, fibrous material such as quartz, or sleeve junctions. Porous materials such as wood, Teflon™, wicks, or ground glass points have also been used.

In U.S. Pat. No. 3,440,525, the use of a large junction surface comprised of wood or a porous ceramic material is disclosed. It turns out that wood in particular is a good material for use because electrolyte contact can be maintained through small capillaries or natural channels which extend axially (in the direction of the wood grain) between the electrolyte and the specimen fluid. Though the use of wood or other porous materials provides an effective liquid junction, it became desirable to extend the life of various electrochemical sensors by prolonging the usefulness of the wood or other fibrous material used in the sensor.

In U.S. Pat. No. RE. 31,333, the use of a combination of larger wooden plugs linked by smaller wooden plugs is disclosed. An adhesive sealant such as epoxy is used to seal the abutting end surfaces of the large plugs prior to assembly. Thus, when the wood plugs are assembled and filled with electrolyte and the epoxy is in place, the path for ion flow is non-linear. In other words, due to the presence of the epoxy barriers, the ions must pass back and forth between a series of non-axially arranged wood plugs.

In U.S. Pat. No. 5,630,921, an electrochemical sensor is disclosed comprised of a first longitudinal series of semipermeable plugs impregnated with an electrolyte, a second series of semipermeable plugs disposed in an overlapping relation ship with the first series with an interlocking fit, and a series of impermeable plugs. Plugs from the second series of semipermeable plugs pass through the impermeable plugs to maintain an ionic path. Thus, though impermeable plugs are used to retard the poisoning of the reference cell, the ionic path is maintained by semipermeable plugs.

In U.S. Pat. No. 6,054,031, a junction for ionic communication is described which is essentially a channel that extends between an inner surface of a housing and an outer surface of an inner body. The channel is designed with a relatively small cross-section for providing ionic continuity, but also provides a very long and tortuous channel length, thus increasing the ion transit time through the channel. By using such a design, the ion exchange between solutions separated by the channel is limited or significantly slowed. This design avoids the problems associated with plugging because the cross-section can be larger than those described in previous designs. Specifically, a helical channel is disclosed that includes these properties.

SUMMARY OF THE INVENTION

The present invention is drawn to a salt bridge for an electrochemical sensor comprising (a) at least two chambers for containing an electrolyte fluid; (b) a plug for separating the at least two chambers, said plug being essentially impermeable to the electrolyte fluid; and (c) a narrow opening through the plug providing a non-axial flow path for ionic communication between the at least two chambers when the electrolyte fluid is present.

In a further detailed aspect of an embodiment of the invention, a salt bridge for an electrochemical sensor can comprise (a) at least two chambers for containing an electrolyte fluid; (b) a plug for separating the at least two chambers, wherein the plug comprises a material essentially impermeable to the electrolyte fluid; (c) an orientation axis defined by the shortest distance between the at least two chambers; and (d) a non-axial narrow opening through the plug with respect to the orientation axis, wherein the non-axial narrow opening defines a non-axial flow path between the at least two chambers, wherein at least a section of the non-axial flow path is within the non-axial narrow opening, and wherein the non-axial flow path provides ionic communication between the at least two chambers when the electrolyte fluid is present in the at least two chambers.

Additionally, a separation device for separating multiple chambers within an electrochemical reference cell is disclosed comprising (a) a first fluid impermeable barrier having a fluid directing surface and including at least one open channel for allowing ionic communication between the multiple chambers when a continuous electrolyte fluid is present; and (b) a second fluid impermeable barrier having a fluid blocking surface mated against the fluid directing surface such that the open channel is closed to form a tunneled flow path.

Further, a separation device for separating multiple chambers within an electrochemical reference cell can also comprise (a) a first fluid impermeable barrier having a fluid directing surface and including at least one open channel for allowing ionic communication between the multiple chambers when a continuous electrolyte fluid is present; and (b) a second fluid impermeable barrier having a fluid blocking surface mated against the fluid directing surface such that the open channel is closed to form a fluid flow path, wherein the first and second fluid impermeable barriers are configured in the shape of discs, each having axially centered bores, and wherein one of the discs has a larger outer diameter and a larger bore diameter than the opposing disc.

Each of these embodiments are preferably used within an electrochemical sensor for measuring ionic properties of a fluid specimen. Such a device is preferably comprised of a reference cell having a first chamber proximal to the fluid specimen desired to be measured; a second chamber distal to the fluid specimen; an essentially impermeable plug for separating the first chamber from the second chamber; a non-axial flow path through the plug which fluidly connects the first chamber to the second chamber; a continuous electrolyte fluid within the first chamber, the second chamber, and the non-axial flow path; and a liquid junction area for contacting the continuous electrolyte fluid with the fluid specimen. Additionally, an electrolyte sensing element, e.g., metal-metal salt, can be present in the second chamber and in ionic communication with the continuous electrolyte fluid, and a specimen sensing electrode can also be in electrical communication with the electrolyte sensing element such that differences in electrical potential may be measured.

A method of defining pH compared to a reference is also disclosed comprising the steps of (a) establishing a reference cell; (b) contacting a solution specimen with a specimen sensing ion electrode; (c) establishing electron flow between the reference cell and the solution specimen from a first chamber, across a small non-axial ion flow path which penetrates an otherwise impermeable plug, to a second chamber; and (d) measuring any difference in electrical potential.

In a further detailed aspect of an embodiment of the invention, an alternative method of defining pH compared to a reference can comprise (a) establishing a reference cell; (b) contacting a solution specimen with an ion sensor; (c) establishing electron flow between the reference cell and the solution specimen from a first chamber, across a small non-axial ion flow path to a second chamber, wherein the non-axial ion flow path is non-axial with respect to an orientation axis defined by the shortest distance between first chamber and the second chamber, and wherein the non-axial flow path is through a plug comprising an essentially impermeable material which separates the first chamber from the second chamber; and (d) measuring any difference in electrical potential between the reference cell and the solution specimen.

DESCRIPTION OF THE DRAWINGS

In the accompanying drawings which illustrate embodiments of the invention.

DETAILED DESCRIPTION OF THE INVENTION

Before the present invention is disclosed and described, it is to be understood that this invention is not limited to the particular process steps and materials disclosed herein as such process steps and materials may vary to some degree. It is also to be understood that the terminology used herein is used for the purpose of describing particular embodiments only and is not intended to be limiting as the scope of the present invention will be limited only by the appended claims and equivalents thereof.

Figure 1:
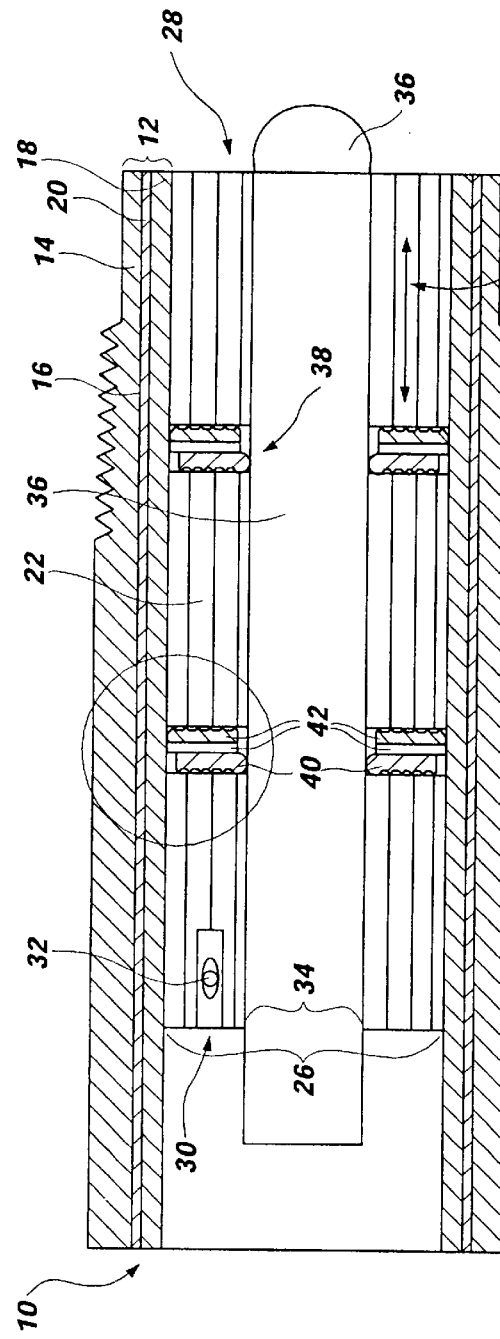
FIG. 1 is a cross-sectional view of an electrochemical sensor embodied in accordance with one aspect of the present invention.

Referring to FIG. 1, a cross-sectional view of an electrochemical sensor 10 is shown. Generally, the sensor 10 is supported by a housing 12 which is comprised of an outer shell 14 having ridges 16 for accepting a sensor protector or cap (not shown), an inner shell 18, and an isolation solution ground path 20. The outer shell 14 is cylindrically shaped and can be made from a rigid material which is inert or otherwise chemically compatible with the specimen fluid to be tested. Polyvinylidene fluoride plastic is an exemplary material having such properties, though other materials may be used as would be known by those having ordinary skill in the art. The inner shell 18 can likewise be comprised of a material having structural rigidity and which is inert or otherwise chemically compatible with the specimen fluid to be tested as well as the electrolyte solution which it directly contacts.

Within the inner shell 18 are three semipermeable plugs 22 which are configured in the shape of rings. These semipermeable plugs 22 are preferably constructed of a wood such that the grain generally follows an axial path 24. An outer diameter 26 of the semipermeable plugs 22 is preferably snugly pressed against an interior surface of the inner shell 18 such that any electrolyte (not shown) or migrated specimen fluid (not shown) can not radially escape the semipermeable plug 22.

The semipermeable plugs 22 are physically separated from one another by one or more channeled impermeable plugs which will be described below. At a proximal end 28 of the device 10, the semipermeable plugs 22 contact the specimen fluid to be tested. At a distal end 30, an electrolyte sensing element 32 is present and in ionic communication with the electrolyte fluid.

Within an inner diameter 34 of the ring-shaped semipermeable plug 22 is a specimen sensing electrode 36. The specimen sensing electrode 36 can fit snugly within the inner diameter 34 of the semipermeable plug 22 such that fluid is not allowed to escape the semipermeable plug 22 radially.

The semipermeable plugs 22 are separated by a pair of impermeable plugs 38 which are configured in the shape of discs having axially centered bores (not shown) therethrough. Specifically, a first impermeable plug 40 and a second impermeable plug 42 are shown which may be seen in further detail in FIG. 2.

Figure 2:
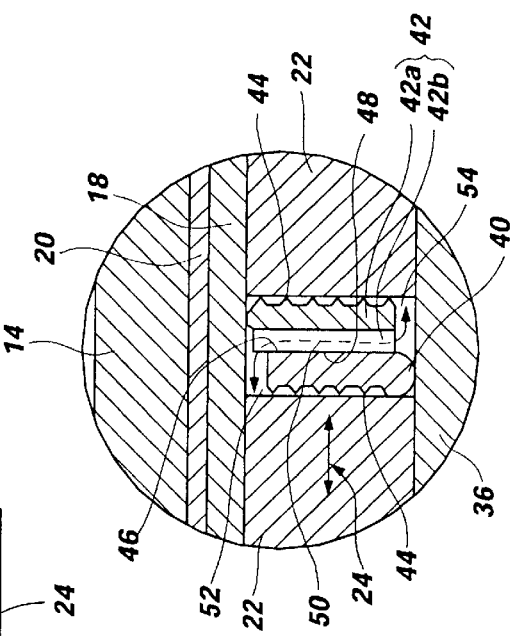
FIG. 2 is cross-sectional view of a portion of FIG. 1.

Turning to FIG. 2, a cross section of one portion of the pair of impermeable plugs 38 is shown. Specifically, the first impermeable plug 40 is defined by two surfaces. One surface has a series of ridges 44 positioned concentrically which press into the semipermeable plug 22 such that any poisons that migrate into the semipermeable plug are refrained from substantially migrating radially. Opposite the concentric ridges 44 is a flat surface 46 which acts to block electrolyte from escaping the open channel as will be described below.

The second impermeable plug 42 is generally comprised of two sections 42a, 42b. Section 42a and section 42b are joined to form the second impermeable plug 42. Though the second impermeable plug 42 is shown in two sections 42a, 42b, one skilled in the art would recognize that the second impermeable plug need not be divided into two sections, but may be one integrated plug. Similar to the first impermeable plug 40, the exposed surface of section 42a has a series of concentric ridges 44 which press into the semipermeable plug 22 such that any poisons that migrate into the semipermeable plug are refrained from substantially migrating radially. Opposite the concentric ridges 44, and on section 42b, a fluid directing surface 48 is present for directing fluid in a non-axial direction to form a non-axial flow path 50. The flat or blocking surface 46, the surfaces having concentric ridges 44, and the fluid directing surface 48 may be seen more clearly in FIGS. 3 and 4.

A first opening 52 and a second opening 54 are also shown. The first opening is defined radially by the inner shell 18 and the first impermeable plug 40, and axially by a semipermeable plug 22 and the second impermeable plug 42. The second opening is defined radially by the second impermeable plug 42 and the specimen sensing electrode 36, and axially by a semipermeable plug 22 and the first impermeable plug 40.

In the design of the present embodiment, the first impermeable plug 40 has an axial bore (not shown) that snugly fits around the specimen sensing electrode 36 providing an essentially sealed fit. The exterior diameter (not shown) of the first impermeable plug 40 is configured to leave a gap or opening 52 near the inner shell 18. Conversely, the second impermeable plug 42 is designed such that the exterior diameter (not shown) fits snugly against the inner shell 18 to provide an essentially sealed fit. Additionally, the inner bore (not shown) is configured to leave a gap or opening 54 near the specimen sensing electrode 36. Thus the exterior diameter and the bore of the first impermeable plug 40 are both smaller than the exterior diameter and the bore of the second impermeable plug 42 respectively. However, though the first impermeable plug 40 is described being generally smaller with respect to the outer diameter and the central bore, one skilled in the art would recognize that impermeable plugs 40, 42 could be changed in size such that the first impermeable plug is generally larger with respect to the outer diameter and the central bore. In other words, the first impermeable plug could act to seal against the inner shell of the housing and the second impermeable plug could act to seal against the specimen sensing electrode without altering the basic function. Thus, the first impermeable plug 40 is described to be smaller merely for convenience. However, all that is preferred for this particular embodiment is that the impermeable plugs 40,42 be different in size such that one seals against the inner shell 18 and the other seals against the specimen sensing electrode 36.

Figure 3:
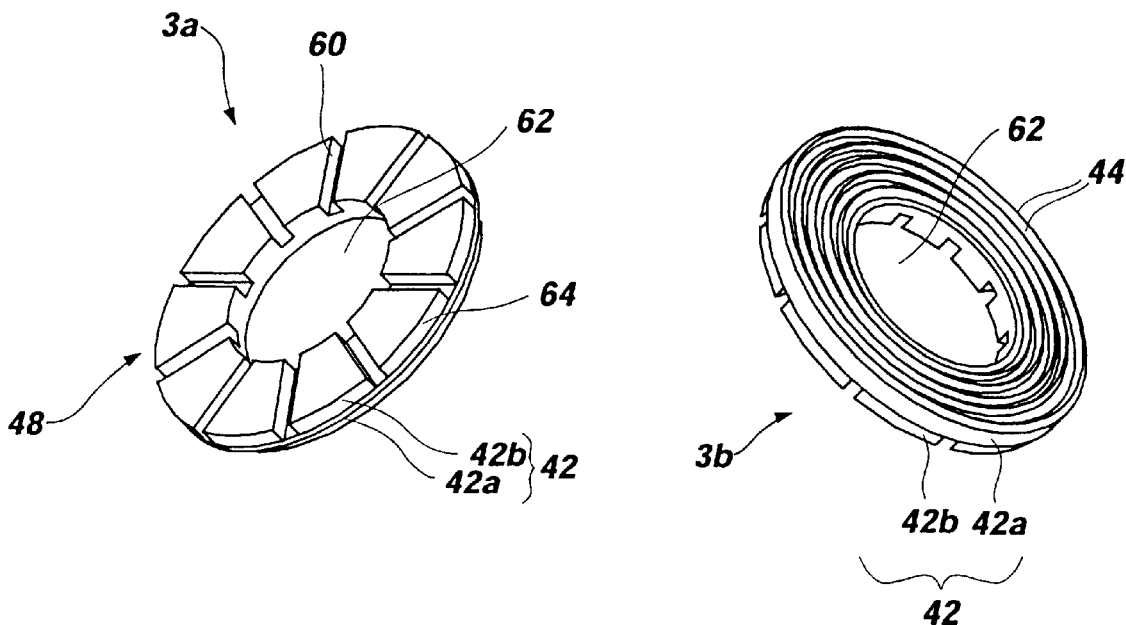
FIG. 3 shows two perspective views (3a and 3b) of a first impermeable plug or barrier having a fluid directing surface and a concentric ring surface.

Turning now to FIG. 3, a first view 3a and a second view 3b are shown. In the first view 3a, section 42b is generally shown. On section 42b is a fluid directing surface 48 comprised of a series of open channels 60 which are radially configured between a central bore 62 and an exterior diameter 64. In the second view 3b, section 42a is generally shown. On section 42a is a surface having concentric ridges 44 for preventing any poisons that may migrate into the semipermeable plug from migrating radially, and thus, contaminate the open channels 60.

Figure 4:
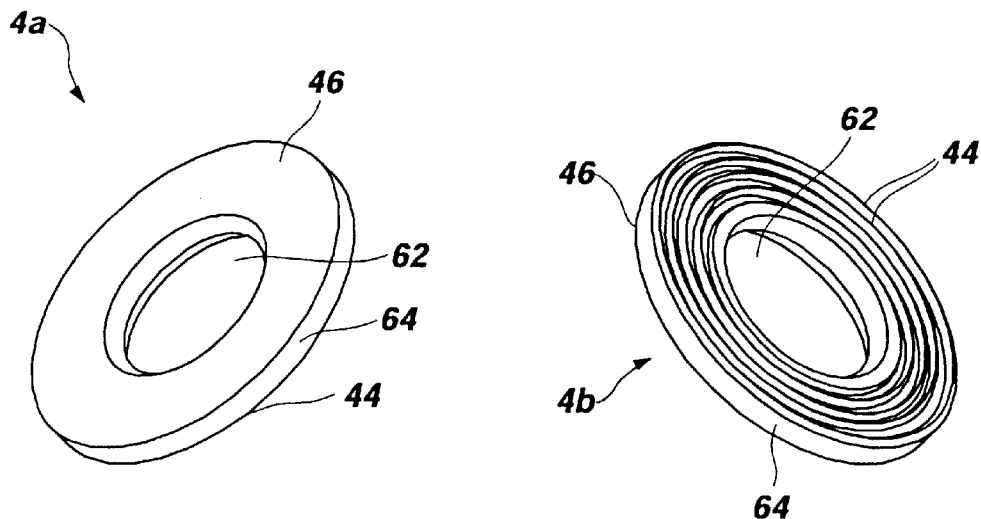
FIG. 4 shows two perspective views (4a and 4b) of a second impermeable plug or barrier having a fluid blocking surface and a concentric ring surface.

In FIG. 4, a first view 4a and a second view 4b are shown. In the first view 4a, a blocking surface 46 is shown. The blocking surface 46 shown in view 4a is generally pressed against the fluid directing surface 48 (shown in view 3a) to prevent fluids from escaping from the open channels 60.

Thus, the blocking surface 46 and the fluid directing surface 48 work synergistically to provide radially extending tunneled channels by which fluid may flow. View 4b shows a surface having concentric ridges 44. This surface acts similarly as described previously with respect to view 3b.

With these figures in mind, a salt bridge for an electrochemical sensor comprising (a) at least two chambers for containing an electrolyte fluid; (b) a plug for separating the at least two chambers, said plug being essentially impermeable to the electrolyte fluid; and (c) a narrow opening through the plug providing a non-axial flow path for ionic communication between the at least two chambers when the electrolyte fluid is present. Additionally, electrochemical sensor for measuring ionic properties of a fluid specimen is also disclosed. Such a device is preferably comprised of a reference cell having a first chamber proximal to the fluid specimen desired to be measured; a second chamber distal to the fluid specimen; an essentially impermeable plug for separating the first chamber from the second chamber; a non-axial flow path through the plug which fluidly connects the first chamber to the second chamber; a continuous electrolyte fluid within the first chamber, the second chamber, and the non-axial flow path; and a liquid junction area for contacting the continuous electrolyte fluid with the fluid specimen. An electrolyte sensing element can be present in the second chamber and in ionic communication with the continuous electrolyte fluid. Additionally, a specimen sensing electrode can also be in electrical communication with the electrolyte sensing element such that differences in electrical potential may be measured. In each of these embodiments, the non-axial flow path preferably comprises a linear path, though other non-axial flow paths may be used, e.g., helical, zig-zag, etc. The non-axial flow path is also preferably confined within the body of the plug. Additionally, to avoid the problems associated with plugging, a relatively large opening and/or multiple ion flow paths may be configured within the plug.

The essentially impermeable plug is preferably comprised a first barrier having a fluid directing surface and a second barrier having a fluid blocking surface. Thus, the fluid directing surface and the fluid blocking surface can be mated such that a tunneled non-axial flow path is formed. Most preferably, the first barrier and the second barrier are a pair of discs, each having axially centered bores. In this embodiment, one of the discs has a larger outer diameter and a larger bore diameter than the opposing disc, providing openings to each end of the flow path. Further, the fluid directing surface is preferably comprised of an array of radially symmetrical open channels extending from the bore to the outer diameter. Thus, if one open channel were to become blocked, then others would maintain ionic communication in the presence of an electrolyte solution.

The reason for the different sized discs having different sized axially centered bores is so that openings can be formed between the a housing near the outer diameter and the specimen sensing ion electrode near the bores. For example, the housing and the specimen sensing ion electrode can be concentrically positioned such that the bore of each of the discs is large enough to allow the specimen sensing ion electrode to pass therethrough, and the outer diameter of each of the discs is large enough to fit within the housing. In this embodiment, one of the pair of discs can fit snugly against the specimen sensing ion electrode and the opposing disc can fit snugly against the housing. Therefore, the pair of discs provide a mechanism to seal one chamber for containing electrolyte from the other, i.e., one disc seals at the housing, the other disc seals at the specimen sensing ion electrode, and the pair of discs join one another except for at the open channels where tunneled ion flow paths remain.

Though not required, the chambers containing electrolyte fluid can contain semipermeable plugs impregnated with the electrolyte as described in U.S. Pat. No. RE. 31,333, which is incorporated herein by reference. Various wood materials are useful as semipermeable plugs as they contain natural axial channels for electrolyte and specimen fluids to flow. In addition, the present invention is useful over much of the prior art in that if semipermeable plugs are used, they may be impregnated with electrolyte solution prior to assembly. This allows a more simplified manufacturing process.

Either of the impermeable barriers may further comprise a surface having a series of concentric ridges which press into one of the semipermeable plugs, particularly with respect to the barrier close to the area which contacts the specimen fluid to be tested. This is done such that any poisons that migrate into the semipermeable plug do not substantially migrate to the non-axial flow path or tunneled channel.

A separation device for separating multiple chambers within an electrochemical reference cell is also disclosed which comprises (a) a first fluid impermeable barrier having a fluid directing surface and including at least one open channel for allowing ionic communication between the multiple chambers when a continuous electrolyte fluid is present; and (b) a second fluid impermeable barrier having a fluid blocking surface mated against the fluid directing surface such that the open channel is closed to form a tunneled flow path.

Though not required in the context of the pair of fluid impermeable barriers, the flow path can be non-axial. Additionally, the impermeable barriers described are preferably comprised of elastomeric materials known to be impermeable to fluid. Thus the only place that fluid communication is permitted is through the element flow path. Again, the barriers are preferably in the shape of discs, each having axially centered bores wherein one of the discs has a larger outer diameter and a larger bore diameter than the opposing disc as described previously. Other similar elements that can be present in a preferred embodiment include (a) having an array of radially symmetrical open channels extending from the bore to the outer diameter, (b) having a bore on each of the discs is large enough to allow a specimen sensing ion electrode to pass therethrough, (c) having at least one of the first fluid impermeable barrier and the second fluid impermeable barrier further comprises a second surface having a series of concentric ridges, and as mentioned,(d) having a non-axial flow path.

In addition to the structure disclosed, a method of defining pH compared to a reference is also disclosed comprising the steps of (a) establishing a reference cell; (b) contacting a solution specimen with a specimen sensing ion electrode; (c) establishing electron flow between the reference cell and the solution specimen from a first chamber, across a small non-axial ion flow path which penetrates an otherwise impermeable plug, to a second chamber; and (d) measuring any difference in electrical potential.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

What is claimed is:

1. A salt bridge for an electrochemical sensor comprising:
   (a) at least two chambers for containing an electrolyte fluid;
   (b) a plug for separating the at least two chambers, said plug comprising a material essentially impermeable to the electrolyte fluid;
   (c) an orientation axis defined by the shortest distance between the at least two chambers; and
   (d) a non-axial narrow opening through the plug with respect to the orientation axis, said non-axial narrow opening defining a non-axial flow path between the at least two chambers wherein at least a section of the non-axial flow path is within the non-axial narrow opening, said non-axial flow path providing ionic communication between the at least two chambers when the electrolyte fluid is present in the at least two chambers.

2. The salt bridge of claim 1 wherein the non-axial flow path is linear.

3. The salt bridge of claim 1 wherein the non-axial flow path is confined within the body of the plug.

4. The salt bridge of claim 1 comprising at least two narrow openings through the plug.

5. The salt bridge of claim 1 wherein s aid plug is comprised a first barrier having a fluid directing surface and a second barrier having a fluid blocking surface, said fluid directing surface and said fluid blocking surface being mated such that said non-axial flow path is formed.

6. The salt bridge of claim 5 wherein the first barrier and the second barrier are a pair of discs, each having axially centered bores, and wherein one of the discs has a larger outer diameter and a larger bore diameter than the opposing disc.

7. The salt bridge of claim 6 wherein the fluid directing surface is comprised of an array of radially symmetrical open channels extending from its bore to the outer diameter.

8. An electrochemical sensor for measuring ionic properties of a fluid specimen including the salt bridge of claim 6 further comprising a housing and a concentrically positioned specimen ion sensor, wherein the bore of each of the discs is large enough to allow the specimen ion sensor to pass therethrough, and the outer diameter of each of the discs is small enough to fit within the housing.

9. The electrochemical sensor of claim 8 wherein one of the pair of discs fits snugly against the specimen ion sensor, and wherein the opposing disc fits snugly against the housing.

10. The salt bridge of claim 6 wherein the at least two chambers contain semipermeable plugs impregnated with the electrolyte and said first barrier further comprises a surface having a series of concentric ridges which press into one of said semipermeable plugs, and wherein said second barrier further comprises a surface having a series of concentric ridges which press into a different semipermeable plug, such that any poisons that migrate into the semipermeable plug do not substantially migrate to the non-axial flow path.

11. The salt bridge of claim 1 wherein the at least two chambers contain semipermeable plugs impregnated with the electrolyte.

12. The salt bridge of claim 11 wherein the semipermeable plugs are of wood.

13. The salt bridge of claim 11 wherein the semipermeable plugs are impregnated prior to assembly.

14. A separation device for separating multiple chambers within an electrochemical reference cell comprising:
   (a) a first fluid impermeable barrier having a fluid directing surface and including at least one open channel for allowing ionic communication between the multiple chambers when a continuous electrolyte fluid is present; and (b) a second fluid impermeable barrier having a fluid blocking surface mated against the fluid directing surface such that the open channel is closed to form a fluid flow path, wherein the first and second fluid impermeable barriers are configured in the shape of discs, each having axially centered bores, and wherein one of the discs has a larger outer diameter and a larger bore diameter than the opposing disc.

15. The separation device of claim 14 further comprising an orientation axis defined by the shortest distance between two of the multiple chambers, and wherein said fluid flow path is non-axial with respect to the orientation axis.

16. The separation device of claim 15 wherein said non-axial flow path is linear.

17. The separation device of claim 14 wherein at least one of the first fluid impermeable barrier and the second fluid impermeable barrier comprises elastomeric material.

18. The separation device of claim 14 wherein the fluid directing surface is an array of radially symmetrical open channels extending from its bore to the outer diameter.

19. The separation device of claim 14 wherein at least one of said first fluid impermeable barrier and said second fluid impermeable barrier further comprises a second surface having a series of concentric ridges.

20. An electrochemical sensor for measuring ionic properties of a fluid specimen comprising:

(a) a reference cell having:
  i. a first chamber proximal to the fluid specimen desired to be measured,
  ii. a second chamber distal to the fluid specimen,
  iii. a plug comprising a material essentially impermeable to electrolyte fluid for separating the first chamber from the second chamber,
  iv. a non-axial flow path through the plug, said flow path being non-axial with respect to an orientation axis defined by the shortest distance between the first chamber and the second chamber, and wherein at least a section of the non-axial flow path is within the plug which fluidly connects the first chamber to the second chamber,
  v. a continuous electrolyte fluid within the first chamber, the second chamber, and the non-axial flow path,
  vi. a liquid junction area for contacting the continuous electrolyte fluid with the fluid specimen, and
  vii. an electrolyte sensing element in the second chamber and in ionic communication with the continuous electrolyte fluid; and (b) a specimen sensing electrode in electrical communication with the electrolyte sensing element such that differences in electrical potential may be measured.

21. The electrochemical sensor of claim 20 wherein the non-axial flow path is linear.

22. The electrochemical sensor of claim 20 wherein the non-axial flow path is confined within the body of the plug.

23. The electrochemical sensor of claim 20 further comprising at least two narrow openings through the plug.

24. The electrochemical sensor of claim 20 wherein said plug comprises a first barrier having a fluid directing surface and a second barrier having a fluid blocking surface, said fluid directing surface and said fluid blocking surface being mated such that said non-axial flow path is formed.

25. The electrochemical sensor of claim 24 wherein the first barrier and the second barrier are a pair of discs, each having axially centered bores, and wherein one of the discs has a larger outer diameter and a larger bore diameter than the opposing disc.

26. The electrochemical sensor of claim 25 wherein the fluid directing surface is comprised of an array of radially symmetrical open channels extending from its bore to the outer diameter.

27. The electrochemical sensor of claim 25 further comprising a housing, and wherein the specimen sensing electrode is concentrically positioned within the housing, said electrochemical sensor being further configured such that the bore of each of the discs is large enough to allow the specimen sensing electrode to pass therethrough, and the outer diameter of each of the discs is small enough to fit within the housing.

28. The electrochemical sensor of claim 27 wherein one of the pair of discs fits snugly against the specimen sensing electrode, and wherein the opposing disc fits snugly against the housing.

29. The electrochemical sensor of claim 20 wherein the at least two chambers contain semipermeable plugs impregnated with the electrolyte.

30. The electrochemical sensor of claim 29 wherein the semipermeable plugs are of wood.

31. The electrochemical sensor of claim 29 wherein the semipermeable plugs are impregnated prior to assembly.

32. The electrochemical sensor of claim 29 wherein said first barrier further comprises a surface having a series of concentric ridges which press into one of said semipermeable plugs, and wherein said second barrier further comprises a surface having a series of concentric ridges which press into a different semipermeable plug, such that any poisons that migrate into the semipermeable plug do not substantially migrate to the non-axial flow path.

33. A method of defining pH compared to a reference comprising:

(a) establishing a reference cell;

(b) contacting a solution specimen with an ion sensor;

(c) establishing electron flow between the reference cell and the solution specimen from a first chamber, across a small non-axial ion flow path to a second chamber, wherein the non-axial ion flow path is non-axial with respect to an orientation axis defined by the shortest distance between the first chamber and the second chamber, and wherein the non-axial flow path is through a plug comprising an essentially impermeable material which separates the first chamber from the second chamber; and (d) measuring any difference in electrical potential between the reference cell and the solution specimen.

\* \* \* \* \*